United States Patent [19]
Londesborough et al.

[11] Patent Number: 6,130,368
[45] Date of Patent: *Oct. 10, 2000

[54] TRANSGENIC PLANTS PRODUCING TREHALOSE

[75] Inventors: John Londesborough, Helsinki; Outi Tunnela, Espoo, both of Finland; Kjell-Ove Holmström, Uppsala, Sweden; Einar Mäntylä, Uppsala, Sweden; Björn Welin, Uppsala, Sweden; Abul Mandal, Uppsala, Sweden; Tapio E. Palva, Porvoo, Finland

[73] Assignee: BTG International Ltd, London, United Kingdom

[ * ] Notice: This patent is subject to a terminal disclaimer.

[21] Appl. No.: 08/765,691

[22] PCT Filed: Jun. 29, 1995

[86] PCT No.: PCT/FI95/00377

§ 371 Date: Mar. 18, 1997

§ 102(e) Date: Mar. 18, 1997

[87] PCT Pub. No.: WO96/00789

PCT Pub. Date: Jan. 11, 1996

Related U.S. Application Data

[63] Continuation-in-part of application No. 08/290,301, Aug. 15, 1994, Pat. No. 5,792,921, which is a continuation-in-part of application No. PCT/FI93/00049, Feb. 15, 1993, and a continuation-in-part of application No. 07/841,997, Feb. 28, 1992, Pat. No. 5,422,254, which is a continuation of application No. 07/836,021, Feb. 14, 1992, abandoned.

[30] Foreign Application Priority Data

Jun. 29, 1994 [FI] Finland ..................................... 943133

[51] Int. Cl.$^7$ ............................... A01H 5/00; A01H 5/10; C12N 15/82

[52] U.S. Cl. .......................... 800/298; 800/278; 800/284; 800/287; 800/288

[58] Field of Search .................................. 536/23.2, 23.6, 536/172.3; 435/320.1, 419, 468; 800/205, 250, DIG. 24, DIG. 26, DIG. 67, DIG. 27, DIG. 63, DIG. 9, DIG. 14, DIG. 46, DIG. 52, DIG. 16, DIG. 18, DIG. 41, DIG. 44, DIG. 42, DIG. 23, DIG. 15, DIG. 43, DIG. 25, DIG. 13, DIG. 17, DIG. 65, 278, 288, 284, 287, 298

[56] References Cited

U.S. PATENT DOCUMENTS 5,422,254 6/1995 Londesborough et al. ................ 435/97
5,792,921 8/1998 Londesborough et al. ............. 800/205

Primary Examiner—Amy J. Nelson
Attorney, Agent, or Firm—Kubovcik & Kubovcik

[57] ABSTRACT

The present invention concerns transgenic plants producing trehalose and methods of increasing the trehalose content of plants. According to the invention, the plants of interest are transformed with the coding sequence of a gene for trehalose-6-phosphate synthase fused to a non-constitutive plant promoter, which allows for temporal, topological or stress-induced control over the expression of the gene. The invention can be used for protecting staple crop plants against drought, high salinity or temperature extremes and for improving the storage properties of harvested plants including green food stuffs, picked fruits and ornamental plants.

22 Claims, 7 Drawing Sheets

TRANSGENIC PLANTS PRODUCING TREHALOSE

This application is the national stage filing of PCT/FI95/00377 filed Jun. 29, 1995, which is a continuation-in-part of application Ser. No. 08/290,301 filed Aug. 15, 1994, now U.S. Pat. No. 5,792,921, which is a continuation-in-part of PCT/FI93/00049 filed Feb. 15, 1993, and a continuation-in-part of application Ser. No. 07/841,997, filed Feb. 28, 1992, now U.S. Pat. No. 5,422,254, which is a continuation of application Ser. No. 07/836,021 filed Feb. 14, 1992 now abandoned.

FIELD OF THE INVENTION

The present invention relates to the genetic engineering of plants to introduce a capacity to synthesise trehalose. In particular, the invention concerns plants having an increased trehalose content and methods for producing them. The present invention also relates to methods for increasing the tolerance of plants towards stresses such as cold and drought, as well as to methods for producing trehalose.

BACKGROUND OF THE INVENTION

Trehalose ($\alpha$-glucopyranosyl-$\alpha$-D-glucopyranose) is a dimer of glucose molecules linked through their reducing groups. Because of its unusual combination of chemical properties compared to other sugars, including its lack of reducing groups, slow hydrolysis and ability to form a non-deliquescent glass, it is one of the most effective known preservatives of proteins, cellular membranes and other biological compounds in vitro. Also, living organisms that contain large amounts of trehalose are characteristically those often exposed to osmotic, dehydration and heat stresses, such as insects, certain litoral animals and many microorganisms, including yeasts and bacteria. There is circumstantial evidence (summarised by Wiemken [1990] Antonie van Leeuwenhoek 58, 209–217) that the primary role of trehalose in baker's yeast is to confer resistance to these stresses. However, it has also been suggested (Nwaka et al [1994] FEBS Letters 344, 225–228; Van Dijk et al [1995] Applied Environ. Microbiol. 61, 109–115) that the accumulation of trehalose in baker's yeast is not, by itself, sufficient to confer stress-tolerance.

High levels of trehalose occur in the so-called resurrection plants, such as the pteridophyte, *Selaginella lepidoqhylla*, which can survive prolonged desiccation and heat exposure (reviewed by Avigad [1982] in Encyclopedia of Plant Research (New Series) 13 A, pp 217–347). The great majority of vascular plants, however, are unable to synthesise trehalose. Such plants often accumulate other "compatible" solutes, including glycine betaine, proline and various polyols, in response to stresses such as drought that decrease the availability of intracellular water (reviewed by McCue & Hanson [1990] Trends in Biotechnology 8, 358–362).

There are very few reports of trehalose in angiosperms, and these usually describe small amounts that could reflect microbial contamination (e.g., Kandler & Senser [1965] Z. Pflanzenphysiol. 53, 157–161; Oesch & Meier [1967] Phytochemistry 6, 1147–1148). Indeed, it has been suggested that trehalose is toxic to many plant tissues (Veluthambi et al. [1981] Plant Physiol. 68, 1369–1374), especially those with little or no trehalase activity (trehalase is the enzyme that converts trehalose to glucose). However, at least one angiosperm, *Myrothamnus flabellifolia* (another "resurrection" plant), accumulates significant amounts of trehalose (Bianchi et al. [1993] Physiologia Plantarum 87, 223–226), showing that there is not an absolute compatability barrier between trehalose and angiosperms.

The absence of trehalose from most angiosperms and reported toxicity in some suggests that introduction of a trehalose synthetic pathway into these plants might sometimes have deleterious effects. On the other hand, successful production of trehalose in plants would have substantial advantages. Trehalose accumulated in, e.g., the storage organs of sugar beet, potato, onion etc, could be commercially extracted to provide trehalose at costs that make it competitive with sucrose in certain applications. These applications include the manufacture of dried foods (milk and egg powders, soups, fruit purées, etc), because trehalose preserves the flavour and texture of many food stuffs through economically attractive drying procedures, and is much superior in this regard to sucrose (see, e.g., Roser [1991] Trends in Food Science & Technology, July issue, pp. 166–169; Roser & Colaqo [1993] New Scientist, May issue, pp. 25–28). Compared to sucrose, the non-sweetness of trehalose is a further advantage in many cases (soups, egg powders), as is the fact that it does not yield fructose, which is perceived as a health risk. However, the high price of trehalose makes its use in the dried food industry prohibitively expensive. Secondly, production of trehalose in the edible portion of certain plants could extend the shelf life of products such as tomatoes. Thirdly, accumulation of trehalose in sensitive tissues could increase the tolerance of plants towards frost, drought, high salinity and similar stresses.

SUMMARY OF INVENTION

Based on what has been stated above, it is an object of the invention to provide plants having a novel capacity to synthesise trehalose. In particular, it is an object of the invention to provide controlled accumulation of trehalose in plant tissues as a commercial source of trehalose or to provide stress-tolerance or both, whilst minimising potentially deleterious effects of the trehalose on plant growth.

The present invention is based on the concept of transforming the plants of interest with structural genes for trehalose synthesis under the control of appropriate plant promoters in order to produce transgenic plants having increased trehalose contents. In particular, the coding sequences of one or more genes encoding polypeptides of enzymes producing trehalose 6-phosphate or trehalose itself are, according to the invention, expressed in plants under the control of specific kinds of plant promoters.

Thus, the plant of interest is transformed at least with the coding sequence of a gene for trehalose-6-phosphate synthase (Tre6P synthase) fused appropriately to a plant promoter so that full expression of the gene is realised only as the plant matures or when it encounters specific environmental conditions. The promoters are therefore preferably non-constitutive and chosen to allow temporal (e.g., diurnal), topological (e.g., tissue-specific) or stress-activated (or "stress-induced") control over the expression of the genes. The plant may be also transformed with one or more genes encoding a trehalose-6-phosphatase (Tre6Pase) or a regulatory polypeptide that interacts with the Tre6P synthase or the Tre6Pase or both.

Transformation of the plant may be done by any of the methods available in the art, including infection with tranformed *Agrobacter tumefaciens* and the direct introduction of foreign DNA by microinjection, electroporation, particle bombardment and direct DNA uptake. The structural genes are preferably selected from the group comprising the yeast genes TPS1, TPS2 and TSL1 encoding respectively the 56 kDa Tre6P synthase, 102 kDa Tre6Pase and 123 kDa regulatory subunits of yeast trehalose synthase.

It is another object of the invention to provide a method for producing transgenic plants with increased trehalose contents, which method comprises the steps of transforming a plant of interest with the structural genes for trehalose synthesis, in particular a gene for Tre6P synthase, as mentioned above, and expressing those genes under the control of a suitable promoter to allow temporal, topological, or stress-induced control over the expression of the genes.

It is a third object of the invention to produce trehalose, which comprises the steps of
- transforming a plant with at least one structural gene for Tre6P synthase in order to produce a transgenic plant,
- cultivating the transgenic plant under conditions which will induce the expression of trehalose synthesis in the plant, and
- extracting the trehalose from the tissues of the plant.

A fourth object of the invention is to provide a method of protecting plants against adverse conditions such as drought, high salinity, temperature extremes and other stresses, which method comprises transforming the plant with at least the coding sequence of a gene for a trehalose-6-phosphate synthase fused appropriately to a plant promoter so that full expression of the gene is not realised until the plant encounters adverse conditions. The plant may optionally be also cotransformed with one or more genes encoding trehalose-6-phosphatase and regulatory proteins that interact with the trehalose-6-phosphate synthase or trehalose-6-phosphatase or both. For example, the invention provides a method of protecting plants bearing berries or other fruits against frost damage to blossom, which comprises transforming the plant with a gene for trehalose-6-phosphatase fused appropriately to a plant promoter so that full expression of the gene is not realised until the plant encounters low temperatures.

A fifth object of the invention is to provide a method of producing transformed ornamental plants that do not require such intensive and expert care as the untransformed plant, which method comprises transforming the plant with a gene for trehalose-6-phosphate synthase appropriately fused to a plant promoter so that the plant contains trehalose in some of its tissues.

DETAILED DESCRIPTION OF THE INVENTION

Figure 1:
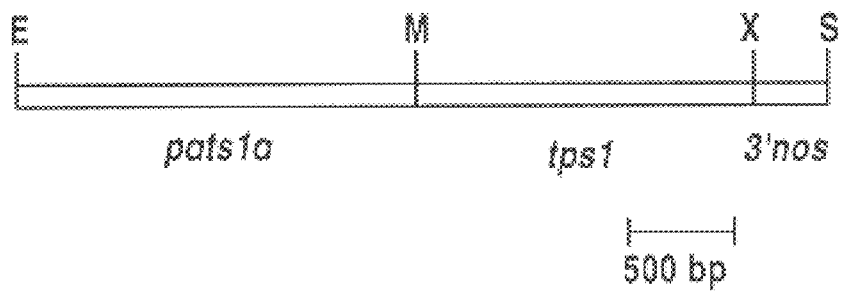
FIG. 1 depicts the schematic structure of the chimeric gene construct containing the *A. thaliana* Rubisco small subunit promoter (pats1A) fused to the TPS1 yeast gene, encoding the Tre6P synthase subunit, and the transcription stop signal from the nopaline synthase gene of *Agrobacterium tumefaciens* (nos). Only the part of the plasmid pKOH51 with the chimeric gene is shown. Unique restriction enzyme cleavage sites for the chimeric gene construction are shown.

In the following description, the phrase "constitutive plant promoter" refers to plant promoters that cause the continuous and general expression of their associated coding sequences, so that the products of these sequences are found in all cells of the plant and at all phases of growth. Non-constitutive promoters, in contrast, are activated by specific internal or external events, such as the differentiation of cells to form distinct tissues as a plant developes and matures or changes in the plant's environment. Many kinds of environmental change are known to activate particular promoters. Examples include the light induced activation of promoters for the small subunit of ribulose-1,5-bisphosphate carboxylase (Krebbers et al. [1988] Plant. Mol. Biol. 11, 745–759), such as the ats1A promoter used in Examples 1–3, and the activation by various stresses of promoters such as LTI78 (Nordin et al. [1993] Plant Mol. Biol. 21, 641–653) and RAB18 (Låang & Palva [1992] Plant Mol. Biol. 20, 951–962). However, our invention is not limited to these examples of non-constitutive promoters. Rather, an important and novel part of the invention is the concept that the constitutive synthesis of trehalose by a plant will always be wasteful and sometimes deleterious, so that the benefits of trehalose production disclosed in this application can best be realised by the use of non-constitutive promoters. By means of these non-constitutive promoters, the biosynthesis of trehalose in transgenic plants can be subjected to temporal control (i.e., it only occurs at certain times), topological control (i.e., it is limited to certain parts of the plant) or both.

The names of plant organs used in this description are generally those applied by the ordinary greengrocer and her customer. Thus, for example, "fruit" includes the parts of an apple or strawberry plant that are sold to be eaten, although these storage tissues containing the seeds are not themselves fruits in a strict botanical sense.

It has already been mentioned that nearly all species of vascular plants appear to lack the ability to synthesise trehalose, so that the term "trehalose-producing" plants does not require quantitative definition. However, the possibility that some ordinary plants (other than the so-called resurrection plants) might produce trehalose during stress appears not to have been investigated. The present invention is concerned with the genetic engineering of plants to introduce a heterologous capacity for trehalose synthesis (in the present context also called a "novel" capacity for trehalose synthesis). The increase in trehalose required, compared to that in the untransformed plant grown under identical conditions, is that which either causes a useful improvement in stress-tolerance or can be profitably extracted from the plant for commercial use.

Many microbial organisms contain enzyme systems that produce trehalose-6-phosphate (Tre6P) and hydrolyse it to trehalose. For example, *Saccharomyces cerevisiae* contains a trehalose synthase complex comprising 56, 102 and 123 kDa subunits (Londesborough & Vuorio [1993] Eur. J. Biochem. 216, 841–848) which condenses uridinediphosphoglucose (UDPG) and glucose-6-phosphate (Glc6P) first to Tre6P (the Tre6P synthase reaction) and then to free trehalose (the Tre6Pase reaction). Tre6P synthase and Tre6Pase activities reside in the 56 and 102 kDa subunits, respectively, and the 123 kDa subunit confers regulatory properties on the complex and appears to stabilise it. Other microbial systems include those of *Candida utilis* (Soler et al [1989] FEMS Microbiol Letters 61, 273–278), *E. coli* (Glaever et al [1988] J. Bacteriol. 170, 2841–2849), *Dictyostelium discoideum* (Killick [1979] Arch. Biochem. Biophys. 196, 121–133) and *Mycobacterium smegmatis* (Lapp et al [1971] J. Biol. Chem. 246, 4567–4579), the latter two systems being able to use adeninediphosphoglucose (ADPG) as an alternative to UDPG. Little information is available about the subunit structure of these other microbial enzyme systems. Multicellular organisms that make trehalose, including nematodes, insects and resurrection plants, may also be assumed to contain enzymes with Tre6P synthase and Tre6Pase activity.

In principle, transfer of any of these Tre6P synthases to plants would give the plants the novel capacity to synthesise Tre6P. It is disclosed that some plants, such as tobacco, have an inherent capacity to convert Tre6P to trehalose, so that, surprisingly, transformation of, e.g., tobacco with a gene for Tre6P synthase alone leads to efficient production of trehalose itself. However, if the endogenous conversion of Tre6P to trehalose is slow or absent, a Tre6Pase from any suitable source may be also transferred. With systems such as the yeast enzyme, where the Tre6P synthase and Tre6Pase are subunits of a trehalose synthase, it may be advantageous to cotransform plants with genes for Tre6P synthase and Tre6Pase from the same source, so that the natural enzyme complex can be formed. Whatever the source of the enzymes, the trehalose formed in the transgenic plants can then be extracted or could confer increased tolerance to certain stresses. The production of trehalose in plants transformed in this way with certain yeast genes has already been described (PCT/FI93/00049).

However, although the accumulation of trehalose at certain times (e.g., during exposure to stress or in a mature plant) and in certain tissues (e.g. storage organs or, at appropriate times, frost-sensitive tissues) is expected to be beneficial, or at least harmless to a plant, there is a distinct possibility that at other times and in other tissues the accumulation of trehalose may be harmful to a plant (Veluthambi et al. [1971] loc cit). It would therefore be advantageous to use a plant promoter (a promoter is a part of a gene that promotes transcription of the coding sequence) that does not permit full expression of the gene(s) causing trehalose synthesis until the plant is mature or encounters environmental conditions, including drought and low temperature, in which the benefits of trehalose outweigh its possible disadvantages to the plant.

Several examples of such non-constitutive plant promoters are known to those familiar with the art, including the small subunit ribulose-1,5-bisphosphate carboxylase (Rubisco) promoter, which drives the light-induced expression of the small subunit of RUBISCO (Krebbers et al. [1988] Plant Mol. Biol. 11, 745–759).

Tobacco and Arabidopsis plants transformed with the coding sequence (open reading frame, ORF) of the yeast TPS1 gene correctly fused to the ats1A promoter of a Rubisco small subunit gene are disclosed. TPS1 encodes the 56 kDa subunit of yeast trehalose synthase. The transformed plants are healthy and fertile and contain trehalose in their leaves. Untransformed tobacco or tobacco transformed with a similar vector lacking the TPS1 gene do not contain trehalose. The disclosed transgenic plants were obtained using A. tunefaciens to mediate the transformation, but any method available in the art may be exploited, including the direct introduction of DNA by microinjection, electroporation or particle bombardment (Gasser & Fraley [1989] Science 244, 1293).

One of these transformed tobacco plants (Transformant 4) is shown to contain Tre6P synthase activity. The free 56 kDa subunit is known to be unstable when isolated from the intact trehalose synthase complex of yeast (Londesborough & Vuorio [1993] loc cit). Methods are described by which a person skilled in the art can co-transform plants with the TPS1 gene and one or both of the other yeast trehalose synthase genes (TPS2 and TSL1) under the control of plant promoters, e.g. the ats1A promoter or some convenient promoter that may be constitutive. Such co-transformation may increase the trehalose content of the plants compared to that of plants containing only TPS1, because the subunits encoded by TPS2 and TSL1 will stabilise the 56 kDa subunit.

In plants cotransformed with a Tre6P synthase gene controlled by an inducible promoter together with one or more genes for Tre6Pase or regulatory proteins (such as the TSL1 product) controlled by constitutive promoters, the production of trehalose will be regulated by the inducible promoter, since Tre6P synthase catalyses the first unique step of trehalose biosynthesis.

It is disclosed that the transformed tobacco plants producing trehalose demonstrate enhanced drought tolerance. This is shown by experiments both with detached leaves and with whole plants. The improved drought tolerance is exhibited by mature plants and by young seedlings of self-pollinated progeny of the transformants. In these progeny, drought tolerance co-segregated with the TPS1$^+$ character as revealed by the presence of the 52 kDa Tre6P synthase subunit in green tissue of the progeny.

The water-stress tolerance of the disclosed transgenic plants is surprising, because the amounts of trehalose found in their tissues seem too small to provide osmotic buffering of the intracellular contents. Possibly the trehalose acts by protecting specific sites, such as membranes, or possibly trehalose or its precursor, Tre6P, perturb the plant's metabolism to cause secondary changes that protect the cells against stress.

It is disclosed that the mild morphological changes seen in the primary transformants containing the chimeric TPS1 gene, such as lancet-shaped leaves, reduced apical dominance and reduced height mainly disappeared in progeny still producing trehalose. These alterations appear to be mainly artefacts due to tissue culture. However, it is disclosed that trehalose-producing tobacco plants, including self-pollinated progeny, grow a little slower, lagging the control plants by 1 to 2 weeks after 8 weeks' growth under optimal conditions. This indicates that the synthesis of trehalose in the plants, even under the control of the ats1A promoter, may slow growth. Thus, stress-induced promoters such as LT178 (Nordin et al [1993] Plant Mol. Biol. 21, 641–653) may be used to further advantage to maintain normal growth rates and yields under non-stressing conditions whilst providing trehalose-induced protection under stress, as explained in Example 5.

These transgenic plants synthesised trehalose although they were transformed with only the yeast TPS1 gene encoding Tre6P synthase, and not with the TPS2 gene, encoding Tre6Pase. Thus, some plants have an endogenous capacity to convert Tre6P into trehalose. It may be advantageous in some cases to cotransform the plant also with a gene, such as TPS2, encoding a Tre6Pase, to increase the rate of conversion of Tre6P to trehalose. Furthermore, it is obvious that similar results may be obtained with genes for Tre6P synthase (and Tre6Pase) obtained from organisms other than yeast. Many of these genes will be homologous to TPS1 (and TPS2) and may be readily cloned using immunological or oligonucleotide probes derived from the enzymes and genes of the yeast system. For example, the Tre6P synthase from *Mycobacterium smegmatis* is disclosed to be an about 55 kDa polypeptide that cross-reacts with anti-serum raised against the purified 56 kDa Tre6P synthase subunit of yeast trehalose synthase. Amino acid sequences of tryptic peptides from the *M. smegmatis* enzyme are disclosed, revealing close sequence homology to the yeast enzyme. A person skilled in the art can readily clone genes for Tre6P synthase and Tre6Pase from many organisms using these approaches. Our invention embraces the transformation of plants with genes for Tre6P synthase and Tre6Pase obtained from any suitable organism, and fused to appropriate plant promoters.

Plants containing trehalose as a result of transformation with one or more genes for trehalose synthase can be used in several ways. For example, trehalose can be extracted from the plants on a commercial scale. Such trehalose would be cheap enough to be used in bulk applications, including the preservation of the flavour and structure of food stuffs during drying. For this application the trehalose would preferably be accumulated in a storage organ, such as the tuber of a potato, the root of a sugar beet or turnip or the bulb of an onion. Methods have been described for the transformation of these examples and many other crop plants (Lindsey [1992] J. Biotechnol. 26, 1–28), but our invention is not limited to those plants that are frequently used as models by molecular biologists. The methods developed for model plants can be adapted by one skilled in the art to other plants. Thus, the present application could also be realised for example, in the stem and leaves of a transformed sugar cane or the fruit of a banana. Plant promoters are known in the art (e.g., the patatin promoter) that cause expression specifically in a storage organ. In one aspect of the present invention, the coding sequence of a gene for Tre6P synthase, such as TPS1, is fused to such a promoter in the same way as the TPS1 coding sequence was fused to the ats1A promoter, and suitable plants are transformed with these DNA constructions. The trehalose accumulated in the storage organs may then be extracted.

Figure 5A:
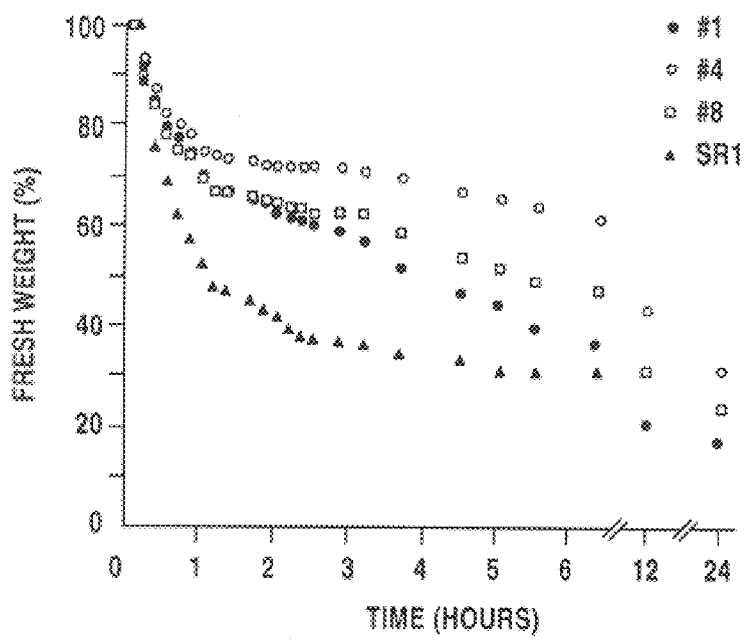
FIGS. 5A–5B. Enhanced drought tolerance in trehalose-producing plants. Detached leaves of same developmental stage from six to eight week-old in vitro propagated plants were exposed to air-drying (25% RH). (A) At times indicated the leaves were weighed and the results presented as relative fresh weight of the leaves at each time point. The dry weight of each leaf was obtained following drying of the leaves at +60° C. for 48 hrs. The wild-type control tobacco is indicated by SR1 and the trehalose-producing transgenic lines 1, 4 and 8 by their respective line numbers. (B) Appearance of the detached leaves from transgenic line 4 and control plants at selected time points during the stress treatment.
Figure 5B:
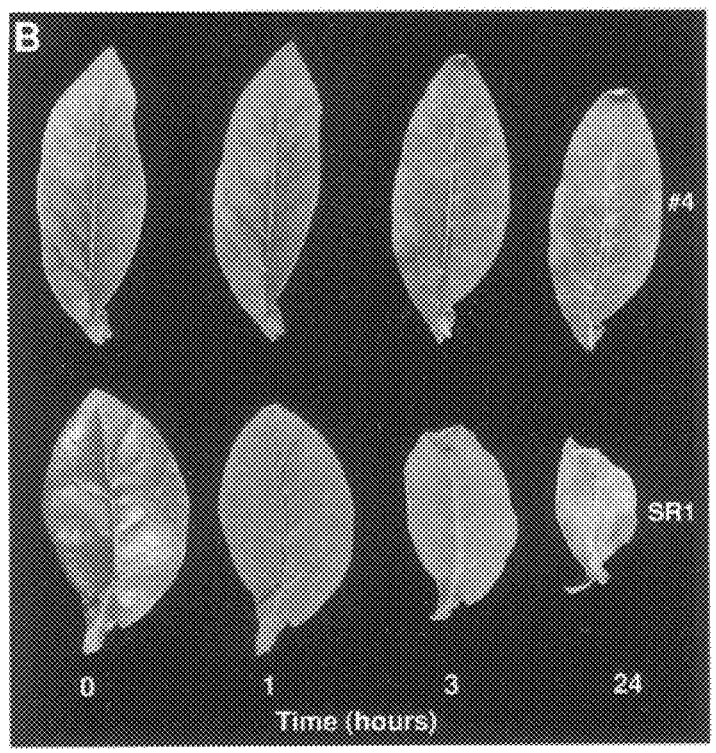

In another aspect of the invention, the trehalose accumulated in the tissues of a plant may improve the storage properties after harvesting. Thus, the detached leaves of transformed tobacco lost water more slowly than those of untransformed tobacco, and even after loosing water did not become discoloured (FIG. 5). This aspect is applicable both to edible plants and to ornamentals. Regarding edible plants, the shrivelling and discolouration of the various kinds of commercial lettuces that occur after harvesting is a serious economic burden especially to retail outlets. The ultimate cost is passed on to the consumer. Trehalose-producing lettuces will provide the consumer with both cheaper and more attractive salads. Similar considerations apply to other food plants, especially leafy products such as cabbages, broccoli, spinach, dill or parsley and other green vegetables such as peas and runner beans. Many ornamentals, such as roses, tulips, daffodils, are transported after cutting. Even with expensive (refrigerated, air freight) transport, much wastage occurs. Again, the cost is carried by the consumer, who will be provided with both cheaper and more delightful products by trehalose-producing ornamentals that better retain their water content and are less susceptible to discolouration. In this aspect of our invention, the Tre6P synthase gene is fused to a plant promoter chosen so that trehalose accumulates in the plant parts to be harvested. For example, the ats1A promoter causes expression of Tre6P synthase in the leaves, upper stem and flower buds of tobacco, and trehalose accumulates in these parts. However, the inventors disclose that plants such as tobacco transport trehalose from its site of synthesis to tissues that do not synthesise trehalose. Thus, smaller amounts of trehalose were also found in the roots of these transgenic tobacco plants, although the non-constitutive ats1A promoter did not cause expression of Tre6P synthase in the roots.

In a related aspect of the invention, edible parts of transformed plants containing trehalose, such as tomatoes, berries and other fruits, are processed to make purees, pastes, jellies and jams that have a fresher and richer flavour because of their trehalose content. It has been shown (WO 89/00012) that adding trehalose to such food stuffs improves the preservation of their flavour, particularly when the processing involves a drying step. The present invention circumvents the need to add trehalose, by providing a plant that already contains trehalose. It may be an advantage in this aspect of our invention to use promoters, such as the patatin promoter, that direct the synthesis of trehalose primarily to the storage organ of the target plant.

It is disclosed that transformed tobacco that produces trehalose has increased drought resistance. In general, transformed plants containing trehalose may be more resistant to drought, frost, high salinity and other stresses than the untransformed plants. Thus, drought, frost and osmotic stress all distress plants primarily by withdrawing water from within cells, so causing damage to membranes and proteins that trehalose is known to alleviate in vitro (Crowe et al [1992] Annu. Rev. Physiol. 54, 579). In this aspect of the invention, the plant promoter used may be one that is induced by stress. Such promoters are known in the art, e.g. LTI78 (Nordin et al. [1993] Plant Mol. Biol. 21, 641–653) and RAB18 (Lång & Palva [1992] Plant Mol. Biol. 20, 951–962). This will prevent the synthesis of trehalose until it is needed. For plants that grow well whilst containing trehalose, this aspect of the invention can be achieved without resource to a stress-induced promoter. However, the use of stress-induced promoters to prevent trehalose production until it is needed has the additional advantages of avoiding the yield penalty that would otherwise result from the diversion of photosynthetic capacity to trehalose synthesis, and avoiding a possible retardation of growth, such as is disclosed for tobacco harbouring the pats1A-TPS1 chimera. This aspect has applications not only for food plants, but also for ornamental plants intended for gardens or indoor display. The transformed stress-tolerant ornamental plants would require less intensive and less expert care than the corresponding untransformed plants. The slower growth of some trehalose-producing plants and minor morphological changes observed at least in the primary transformants may not be a disadvantage with ornamental plants: slower growth and novel appearance can be attractive characteristics especially for indoor ornamentals.

In yet another aspect of the invention, a gene for Tre6P synthase is appropriately fused to a plant promoter (e.g., LTI78 or FAB18) that is activated by a specific event or set of conditions (e.g. cold or drought stress) so that accumulation of commercially extractable amounts of trehalose in the plant can be triggered to occur in the mature plant shortly before harvesting, avoiding any deleterious effects of trehalose on the early development of certain plants.

Based on the above disclosure, the transgenic plants according to the invention can be monocotyledonous plants, such as corn, oats, millet, wheat, rice, barley, sorghum, amaranth, onion, asparagus or sugar cane, or dicotyledonous plants such as alfalfa, soybean, petunia, cotton, sugarbeet, sunflower, carrot, celery, cabbage, cucumber, pepper, tomato, potato, lentil, flax, broccoli, tobacco, bean, lettuce, oilseed rape, cauliflower, spinach, brussel sprout, artichoke, pea, okra, squash, kale, collard greens, tea or coffee.

It is disclosed that the yeast gene TPS1 and its product are compatible with the biochemical machinery of tobacco: the gene was highly expressed and the 56 kDa subunit caused the appearance of trehalose. However, it is known in the art that plant genes often have lower A+T ratios than, e.g., microbial genes, and that the expression level of heterologous genes in plants can be increased by altering the codon usage, particularly near the start of the coding sequence, towards that found in plants (Perlak et al. [1991] 88, 3324–3328). We envisage that these and similar modifications of genes may be useful in the present invention.

It is also well known that natural mutations occur in genes. These and artifical changes in the DNA sequence may alter the amino sequences of the encoded polypeptides. As used herein, the term TPS1 (or TPS2 or TSL1) includes all DNA sequences homologous with TPS1 (or TPS2 or TSL1) that encode polypeptides with the desired functional or structural properties of the 56 kDa (or 102 kDa or 123 kDa) subunit of yeast trehalose synthase. Similarly, the term "genes for Tre6P synthase (or Tre6Pase or regulatory polypeptides)" includes not only such genes as may be readily isolated from natural organisms (for example, by using nucleotide probes designed from the known sequences of TPS1 or of TPS2 or TSL1) but also natural and artificial variants that encode polypeptides with the desired functional and structural properties of the polypeptides encoded by the originally isolated genes.

EXAMPLES

General Materials and Methods

Materials

The plants used were *Nicotiana tabacum* cv. SR1 and *Arabidonsis thaliana* L. Heynh. ecotype C-24.

The yeast genes TPS1 (formerly called TSS1), encoding the 56 kDa Tre6P synthase subunit of trehalose synthase, and TSL1, encoding the 123 kDa regulatory subunit of trehalose synthase, were obtained from the plasmids pALK752 and pALK754 described by Vuorio et al. ([1993] Eur. J. Biochem. 216, 849–861). The yeast gene TPS2 was obtained from a plasmid supplied by Drs Claudio De Virgilio and Andres Wiemken, Botanisches Institut der Universität Basel, Switzerland and containing the TPS2 gene cloned into the SacI site of plasmid YCplac111. This gene (described in De Virgilio et al. [1993] Eur. J. Biochem. 212, 315–323) encodes amino acid sequences derived from the 102 kDa subunit as shown in Table 1 of Vuorio et al. (1993, loc cit). Antisera prepared against yeast trehalose synthase (anti-TPS/P) and the 56 kDa subunit (anti-57K) and general biochemicals were from the sources cited in Vuorio et al. (1993, loc cit). Vacuolar trehalase was partially purified as described by Londesborough & Varimo ([1984] Biochem. J. 219, 511–518) from a suc⁻gal⁻mel⁻ mal yeast strain (ALKO2967) and did not hydrolyse sucrose, maltose or melibiose.

DNA Manipulations

All DNA manipulations were carried out according to established laboratory procedures (Sambrook et al [1989] in Molecular Cloning: A Laboratory Manual, Cold Spring Harbor, N.Y.). The $E.$ $coli$ strains DH5α and MC1061 were used for plasmid preparations. The promoter used to control TPS1 expression came from the ats1A gene of $A.$ $thaliana$, which encodes the small subunit of Rubisco (Krebbers et al [1988] loc cit).

To construct a chimeric ats1A -TPS1 gene the ats1A promoter fragment, lacking the sequence for the transit peptide, was amplified by PCR from the plasmid pGSFR401. Synthetic oligonucleotide primers were used to create an EcoRI site at the 5' end and an XbaI site at the 3' end of the amplified fragment. The PCR amplification product was digested with the appropriate restriction enzymes and, following purification on an agarose gel, ligated into an EcoRI and MluI digested pUC19 plasmid. The yeast TPS1 gene was amplified from the plasmid pALK752 described above. The resulting fragment contained 5' MluI and 3' XbaI sites. After digestion and purification the fragment was ligated behind the pats1A in pUC19. A fragment with the promoter-TPS1 construct was cut out with EcoRI and XbaI and then inserted into a pBluescriptII SK⁺ (Stratagene) derived plasmid carrying the 3' end of the T-DNA gene G7 including its polyadenylation signal and the T-DNA right border. Finally, the entire chimeric gene was inserted as an EcoRI-SacI fragment into the plant transformation vector pDE1001 (Denecke et al. [1992] EMBO J. 11, 2345–2355) containing the chimeric kanamycin resistance gene pNOS-NEO-3'OCS as a selective marker. This resulted in the plasmid pKOH51 carrying the chimeric pats1A -TPS1-3'G7 gene. Constructions were cloned in $E.$ $coli$ strain DH5α by transformation, and then transferred by electroporation (Dower, Miller & Ragsdale [1988] Nucl. Acids Res. 16, 6127–6145) to $Agrobacterium$ $tumefaciens$ (C58C1 rif$^R$) containing the non-oncogenic Ti plasmid pGV2260 (Deblare et al [1995] Nicl. Acids Res. 13, 2777–2788).

Other constructs were made in similar ways.

Growth of Plant Material

For axenic growth, sterilised explants from $Nicotiana$ $tabacum$ (SR1) were planted in glass jars containing solidified MS (Murashige & Skoog [1962] Physiol. Plant 15, 473–497) medium supplemented with 2% sucrose (MS-2). These jars were then placed in a controlled growth environment in a culture chamber where plants were allowed to grow at 22° C. with a 16 h photoperiod. Explants were regularly transferred to new jars and MS-2 medium for a continuous growth of axenic material. Greenhouse plants were grown in soil in pots and watered daily. Transformed $A.$ $thaliana$ plants were first grown axenically in baby-food jars in a controlled environment as described for tobacco above, but were later transferred to soil in pots in the greenhouse for seed production. Seeds from the primary transformants were either directly planted in soil for new seed production or surface sterilised and grown axenically in 24-well tissue culture plates for molecular analysis.

Plant Transformation

Tobacco and $A.$ $thaliana$ were both transformed according to the following protocol, with starting material being excised leaves of tobacco and roots of $A.$ $thaliana$. The transformation and tissue culture were essentially as described by Valvekens et al ([1988] Proc. Natl. Acad. Sci. U.S.A. 85, 5536–5540) with the following modifications. Isolated roots or leaves were preincubated on solidified callus-inducing medium (CIM) for 4 days, roots were cut into small segments (1–2 mm) and leaves were cut into larger pieces (10–20 mm) and transferred into 20 ml liquid CIM. 3', 5'-Dimethoxy-4'hydroxyacetophenone was added (0.2 mg/l ) prior to Agrobacterium (C58C1 rif$^R$) infection. The bacteria used for infection were propagated overnight in YEB medium (Vervliet et al. [1975] J. Gen. Virol. 26, 33–48) containing appropriate antibiotics at 28° C., and collected by centrifugation. The bacterial pellet was then resuspended in 10 mM MgSO4, added to the plant tissue and mixed gently for about 15 min. Excess liquid was poured off and the roots blotted on sterile filter paper. After co-cultivation for 2 days on solid CIM, the plant tissue was rinsed 3–4 times with liquid CIM to wash off bacteria, and transferred to selective shoot induction medium (SIM). After 7 days of growth, explants with differentiated morphogenic sectors were transferred to fresh SIM.

Protein Extraction for Western Analysis

Plant samples of 100–200 mg fresh weight were homogenised with a glass rod in 1.5 ml micro centrifuge tubes with 100 μl of protein extraction buffer (50 mM Tris/HCl pH 7.2, 250 mM sucrose, 5 mM EDTA, 10 mM MgCl$_2$, 1 mM CaCl$_2$, 10 mM β-mercaptoethanol, 1 mM phenylmethylsulfonylfluoride (PMSF), 30 μM pepstatin, 50 μM leupeptin and 15 μM aprotinin. Insoluble material was removed by two centrifugations (13,000 g for 10 min). The protein concentration in the supernatants was measured according to Bradford ([1976] Anal. Biochem. 72, 248–254) using bovine albumin as standard. Equal amounts of soluble proteins were loaded onto SDS-PAGE for immunological studies.

SDS-PAGE and Immunological Techniques

Proteins were separated by SDS-PAGE (Laemmli [1970] Nature 227, 680–685). For detection of proteins immunoblotting was made with the antiserum anti-57 (diluted 1/1000) and an anti-rabbit alkaline phosphatase conjugated second antibody. For Western blotting the proteins were electrophoretically transferred to nitro-cellulose filters and stained with 0.5% Ponceau Red in 5% acetic acid to confirm equal loading of the samples and success of transfer. The filters were subsequently blocked overnight with 5% fat-free dry milk powder and probed and stained by standard methods.

Tre6P Synthase Assays

About 500 mg of frozen plant material was weighed and then ground to a fine powder with a mortar and pestel on solid $CO_2$. The powder was transferred to 0.7 ml of 50 mM HEPES/KOH pH 7.0 containing 1 mM benzamidine, 2 mM MgCl$_2$, 1 mM EDTA and 1 mM dithiothreitol (HBMED) containing 1 mM PMSF, and 10 μg/ml each of pepstatin A and leupeptin and allowed to melt. The resulting homogenate was centrifuged 10 min at 17000 g and the supernatant assayed for Tre6P synthase essentially according to Lapp et al. ([1971] J. Biol. Chem. 246, 4567–4579). Sample (10 μl) was added to 90 μl of reaction mixture containing 40 mM HEPES/KOH pH 7.0, 10 mM MgCl$_2$, 10 mM glucose 6-phosphate, 5 mM fructose 6-phosphate, 5 mM uridine-diphosphoglucose (UDPG) and 1 mg/ml bovine albumin and incubated at 30° C. for the required time. The reaction was stopped by 2 min at 100° C. Sugar derivatives (including any sucrose formed) except for trehalose and trehalose 6-phosphate were destroyed by adding 50 μl 0.6 M HCl and heating for 5 min at 100° C. and then 50 μl of 8% NaOH and heating for 15 min at 100° C. Remaining carbohydrate (i.e., trehalose and trehalose 6-phosphate) were then determined with the anthrone assay (Trevelyan & Harrison [1956] Biochem. J. 63, 23–33).

Trehalose Assays

About 500 mg of frozen plant material was quickly weighed into a glass tube. Hot, distilled water (1 ml) was added and the mixture was boiled for 20 min, the leaf material being broken up at intervals with a blunt glass rod. The liquid phase was collected with a pasteur pipette and the solid re-extracted with 0.5 ml of water. The combined liquid phases were clarified by centrifugation. Combined solid residues were dried to constant weight at 107° C. (the dry weights of leaves averaging 5.1% of the fresh weights). The supernatant was analysed using a Dionex DX-300 liquid chromatograph equipped with a Dionex pulsed electro-chemical detector (PED-2). Samples (20 μl; in triplicate) were injected via a Carbopac PA-1 (4×50 mm) pre-column onto a Carbopac PA-1 (4×250 mm) column and eluted with water at 1 ml/min. The eluate was mixed with post-column reagent (0.6 ml/min of 0.3 M NaOH). Trehalose emerged at about 3 min, well before the glucose and sucrose peaks, which emerged at ca 20 min.

Example 1
Trehalose Production by Tobacco Plants Transformed with the Yeast TPS1 Gene Under the ats1A Promoter.

Tobacco transformants and control plants were grown up both in sterile, "in vitro", conditions and in a greenhouse. Mature transformants had no obvious phenotype compared to the untransformed controls or controls transformed with the vector pDE1001 (lacking TPS1). Leaves were collected at 0900 h, frozen and stored at or below −70° C. prior to analysis.

Figure 2:
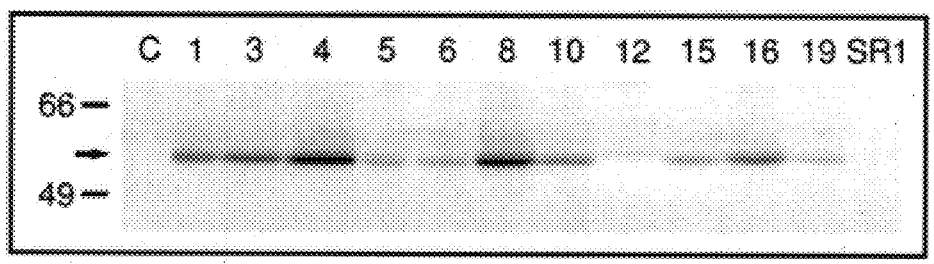
FIG. 2 gives the results of Western blot analysis of transgenic tobacco plants showing the 56 kDa TPS1 product indicated by an arrow. Proteins were extracted from the transformed tobacco plants containing (lines 1, 3, 4, 5, 6, 8, 10, 12, 15, 16 and 19) the construct described in FIG. 1, or (GUS) another chimeric gene with the Cauliflower mosaic virus 35S promoter fused to the β-glucuronidase gene (UIDA) in the same vector or (SR1) from untransformed tobacco plants. Equal amounts of protein were loaded in each lane. The antiserum used (anti-57) was raised against the 56 kDa Tre6P synthase subunit from yeast.
Figure 3C:
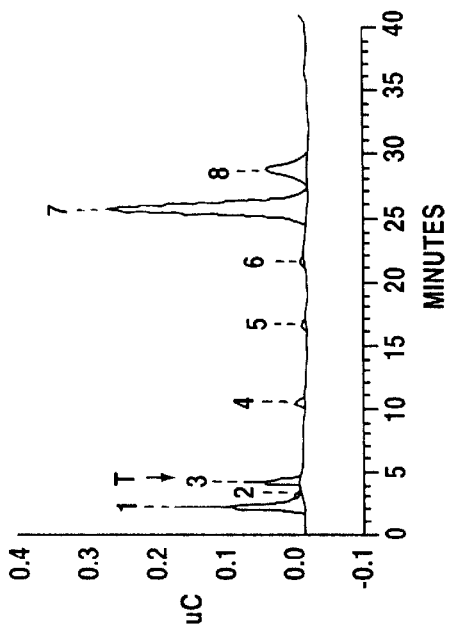
FIGS. 3A–3D show the chromatographic identification of trehalose. Samples (20 µl) of water extracts of tobacco leaves were analyzed by HPLC as described in General Materials and Methods. Extracts A and B contained 192 mg fresh weight of greenhouse-grown Transformant 19 ml$^{-1}$ (A) before and (B) after treatment with trehalase. Extracts C and D contained 149 mg leaf ml$^{-1}$ from (C) Transformant 4 or (D) a control plant transformed with plasmid pDE1001 lacking the TPS1 gene, both grown under sterile conditions. Trehalose peaks are indicated with T. The two large peaks at about 25 min (peaks 7 and 8 in A) are glucose and sucrose.
Figure 3D:
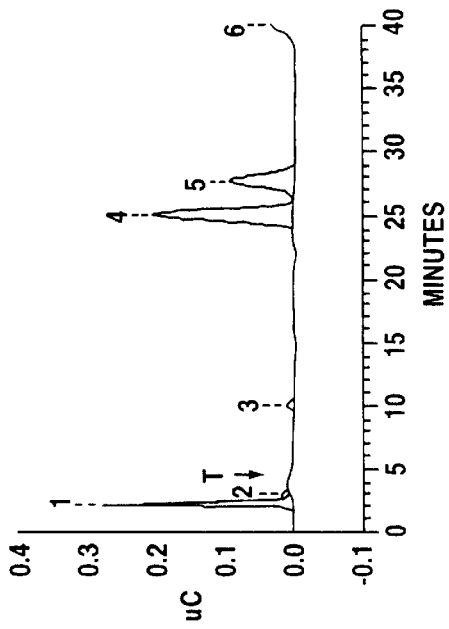
Figure 3A:
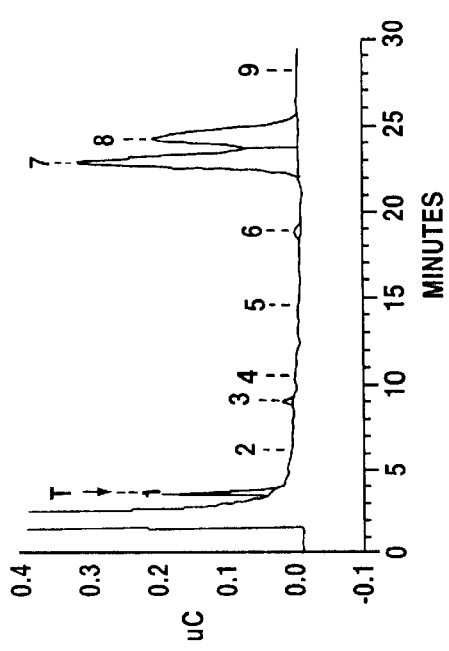
Figure 3B:
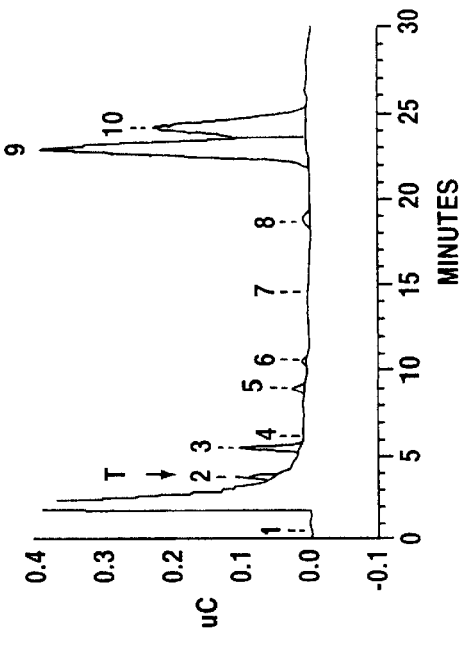

Out of 26 kanamycin-resistant transformants tested, 20 were found to produce detectable levels of immunoreactive polypeptides of the expected size when probed with an antiserum raised against the purified 56 kDa Tre6P synthase subunit of yeast trehalose synthase. Examples are shown in FIG. 2. Table 1 summarises the trehalose contents of the leaves.

TABLE 1

Trehalose contents of TPS1-transformants of tobacco

| Tobacco Plant | Special Treatment | Trehalose (mg/g fresh leaf) |
|---|---|---|
| In vitro plants | | |
| Untransformed SR1 | — | ≧0.002 |
| pDE1001 Control | — | ≧0.002 |
| Transformant 1 | — | 0.02 |
| Transformant 3 | — | 0.009 |
| Transformant 4 | — | 0.067 |
| Transformant 8 | — | 0.075 |
| Transformant 8 | Ethanol extraction instead of water | 0.055 |
| Greenhouse plants | | |
| pDE1001 Control | — | ≧0.002 |
| Transformant 1 | — | 0.16 |

TABLE 1-continued

Trehalose contents of TPS1-transformants of tobacco

| Tobacco Plant | Special Treatment | Trehalose (mg/g fresh leaf) |
|---|---|---|
| Transformant 4 | — | 0.16 |
| Transformant 4 | Alkaline phosphatase[a] | 0.13 |
| Transformant 5 | — | 0.052 |
| Transformant 6 | — | 0.044 |
| Transformant 8 | — | 0.039 |
| Transformant 8 | Specific trehalase | 0.021 |
| Transformant 19 | — | 0.053 |
| Transformant 19 | Alkaline phosphatase[a] | 0.060 |
| Transformant 19 | Specific trehalase | 0.016 |
| Transformant 25 | — | 0.036 |
| Transformant 26 | — | 0.11 |

These results disclose that the yeast TPS1 gene is efficiently expressed in tobacco when its promoter is replaced by the ats1A promoter. The specific signal observed on Western blots has the correct molecular weight. The strongest signals (e.g., that from Transformant 4 grown in vitro) were only slightly weaker per unit of protein applied to the gel than the signals obtained from stationary phase yeast. Expression of TPS1 was accompanied by the appearance of trehalose in the leaf tissue, identified both by its HPLC behaviour and by the fact that it was degraded by a highly specific trehalase (see also FIG. 3). Different transformants expressed the TPS1 product to different levels for reasons that have not yet been established, and (with the apparent exception of Transformant 8) the amount of trehalose found in the leaves roughly correlated with the strength of the 56 kDa signal in the Westerns (compare FIG. 2 with Table 1). Although these transformants did not carry a gene encoding a recombinant Tre6Pase, no evidence was found that the plants accumulated more Tre6P than trehalose. Apparently, tobacco possesses phosphatases capable of converting Tre6P into trehalose, disclosing that for at least this plant, the key enzyme required to introduce a trehalose synthetic pathway is Tre6P synthase, and introduction of this enzyme alone is adequate, though not necessarily optimal.

Figure 4:
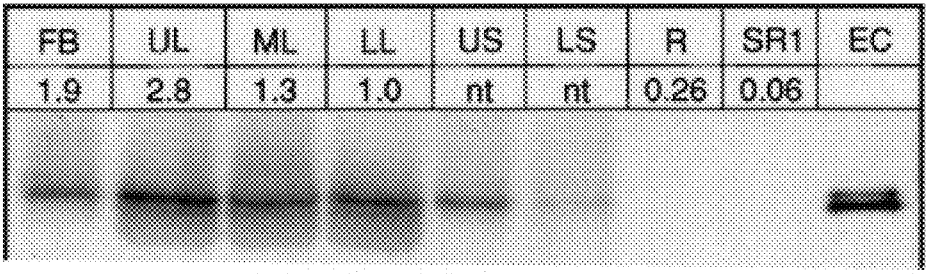
FIG. 4 Protein immunoblot showing tissue localization of TPS1-subunit analyzed in the ats1-TPS1 transformed line 4. Leaves of wild-type tobacco (SR1) were used as a negative control and 0.1 µg of Tre6P synthase subunit purified from yeast (TPS1) as a positive control. The trehalose content of the same tissues is indicated in mg/g dry weight above the immunoblot. nt, not tested. The following abbreviations are used: FB for flower buds, UL for upper leaves, ML for middle leaves, LL for lower leaves, US for upper stem, R for roots and EC for enzyme control.

Determination of the tissue distribution of the 56 kDa Tre6P synthase subunit in transgenic line 4 showed that substantial amounts of this polypeptide could be found in all green parts of the plant except the lower stem, but not in the roots (FIG. 4). This distribution is in accord with the tissue specificity of ats1A gene expression (De Almeida et al [1989] Mol. Gen. Genet. 218, 78). FIG. 4 also shows that tissues in which Tre6P synthase was expressed also contained trehalose. In addition, smaller amounts of trehalose were found in the roots, indicating that transgenic tobacco transports trehalose from its site of synthesis to other tissues.

The results also disclose that tobacco plants expressing TPS1 under the ats1A promoter and accumulating trehalose in their green tissues during daylight are healthy and normal in appearance. Although primary transformants containing the chimeric TPS1 gene had some minor morphological alterations, such as lancet-shaped leaves, reduced apical dominance and reduced height (see FIGS. 5 & 6), most of the changes were not exhibited in self-pollinated TPS1-positive progeny that still produced trehalose (see FIG. 6). Thus, the morphological changes in the primary transformants appear to be artefacts of the tissue culture rather than results of trehalose production. High level production of the Tre6P synthase subunit and the presence of trehalose did, however, lead to a 20 to 50% decrease in the growth rate under normal conditions of the transgenic plants compared to untransformed controls. The apparently normal phenotype of these transgenic plants is in contrast to the reported toxicity of exogenously added trehalose to certain plants (Veluthambi et al [1981] loc.cit.). These results disclose that in planta production of trehalose under the control of the ats1A promoter is not toxic to tobacco, although it may contribute to some reduction in growth rate. Inducible promoters triggered by specific events, including drought or cold, may be used to minimise the reduction in growth rate, by causing the production of trehalose only when it is needed.

On a protein basis, the trehalose contents of the best transformants in Table 1 (e.g. ≧16 mg/g protein for Transformant 4) are already at least 20% of the level at which a clear improvement in thermotolerance is observed in yeast (De Virgilio et al [1990] FEBS Letters 273, 107–110).

Some TPS1-transformants and controls were assayed for Tre6P synthase activity. The results shown in Table 2 are means ∓ the extreme ranges from duplicate zero and 15 or 30 min assays. For the controls, Tre6P synthase activity did not differ from zero. For Transformant 4, an acid- and alkali-stable carbohydrate accumulated in the presence of UDPG and Glc6P. This accumulation required Glc6P, but not fructose 6-phosphate (Fru6P; this hexose phosphate activates the native trehalose synthase complex of yeast) and was prevented when UDPG was replaced by ADPG (the enzyme purified from yeast also cannot use ADPG). The accumulated carbohydrate is presumably trehalose or Tre6P, because other possible products are destroyed by the hydrolyses. HPLC analysis showed it was not trehalose. Thus, under these in vitro assay conditions, Tre6P is synthesised by extracts of Transformant 4 faster than it is converted to trehalose. This shows that the overall rate of trehalose synthesis in the leaves may be increased by cotransformation with TPS2, which encodes the Tre6Pase subunit.

The Tre6P synthase activity of yeast extracts found by the method used in Table 2 agreed with that found by measuring the appearance of UDP as described by Londesborough & Vuorio ([1991] J. Gen. Microbiol. 137, 323–330). Furthermore, yeast extracts measured in the presence of extracts of tobacco plants were not inhibited. Thus, the absence of activity in the control plants in Table 2 is not due to interference by some factor present in tobacco extracts.

TABLE 2

Tre6P synthase activity of TPS1-transformed and
control tobacco leaves (All results are with
plants grown under sterile conditions in vitro).

| Transformant | Assay Mixture | Tre6P Synthase Activity (mU/g fresh leaf) | |
|---|---|---|---|
| | | 15 min | 30 min |
| Untransformed Control | Complete | 3 ± 47 | 3 ± 21 |
| PDE1001 Control | Complete | 22 ± 35 | 7 ± 8 |
| Transformant 4, Expt. 1 | Complete | 259 ± 147 | 60 ± 6 |
| Transformant 4, Expt. 2 | Complete | 128 ± 39 | 155 ± 22 |
| | Less G1c6P | 12 ± 19 | −1 ± 12 |
| | Less Fru6P | 153 ± 10 | 144 ± 3 |
| | ADPG instead of UDPG | 0 ± 52 | 4 ± 21 |

The Tre6P synthase activity found in Transformant 4 was labile. With some extracts, the activity disappeared during a few hours storage on ice. However, the specific band seen in Western analyses was still present at nearly its original strength in extracts stored for 24 h at room temperature. Thus, it is probable that the conformation of the Tre6P synthase subunit changes during storage of tobacco extracts. These results indicate that increased Tre6P synthase activity will be achieved by transforming the tobacco simultaneously with TPS1 and one or more of the other subunits of yeast trehalose synthase, thereby increasing the conformational stability of the Tre6P synthase subunit.

Example 2

Transgenic *Arabidopsis thaliana*

Figure 10:
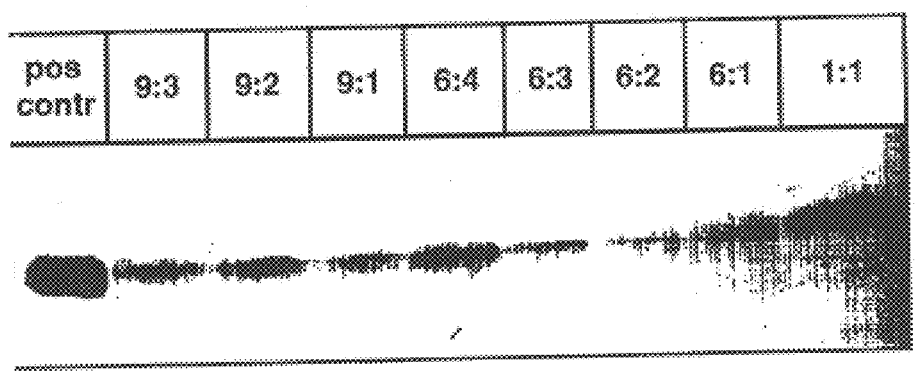
FIG. 10. Western analysis of 8 transgenic lines of *Arabidopsis thaliana*. Plants grown from seed of primary transformants were extracted and analyzed with antiserum raised against the 56 kDa Tre6P synthase subunit from yeast essentially as described in FIG. 2. Tre6P synthase subunit purified from yeast (0.1 μg) was used a positive control. Untransformed *A. thaliana* gives no signal.

*A. thaliana* plants containing TPS1 under the ats1A promoter were constructed in the same way as the tobacco transformants described above. These transformed Arabidopsis plants are also healthy and normal in appearance and produced fertile seed. Western analysis of plants grown up from seeds of the primary transformants showed that they contained the 56 kDa subunit of yeast trehalose synthase (FIG. 10). It is an obvious expectation that these plants accumulate trehalose in their green tissues.

Example 3

Dry Resistance of Trehalose-producing Tobacco Plants

To determine whether the amounts of trehalose produced in the transgenic tobacco were sufficient to enhance their drought tolerance, detached leaves from in vitro propagated control and transgenic lines were subjected to air drying (25% relative humidity, RH) (FIG. 5). Whereas detached leaves of control plants rapidly lost water and showed clear signs of browning after 3 hours of stress, the leaves of trehalose-producing plants remained green up to 24 hours with initially clearly decreased water loss. Thus, the protective effect of trehalose appears two-fold: First detached leaves from transgenic plants synthesizing trehalose appeared initially to have improved water retention. Only after prolonged drought treatment did this difference between trehalose-producing and control plants disappear. Secondly, the control leaves exhibited clear signs of senescence and browning. In contrast, the leaves from trehalose-containing plants appeared green at least for 24 hours and only extended drought exposure (for several days) resulted in some browning. There was a clear difference between trehalose-producing plants and control plants, even at the same water content. Thus, trehalose appears to protect the plant tissue from the effects of dehydration, as well as decreasing the rate of water loss. The browning could at least partly be due to the Maillard reaction where reducing sugars react with free amino groups of polypeptides and amino acids producing a brown colour. As a nonreducing sugar trehalose does not participate in this reaction and it even inhibits the reaction between other sugars and proteins (Roser & Colaco [1993]) New Scientist 1873, 24).

Figure 6A:
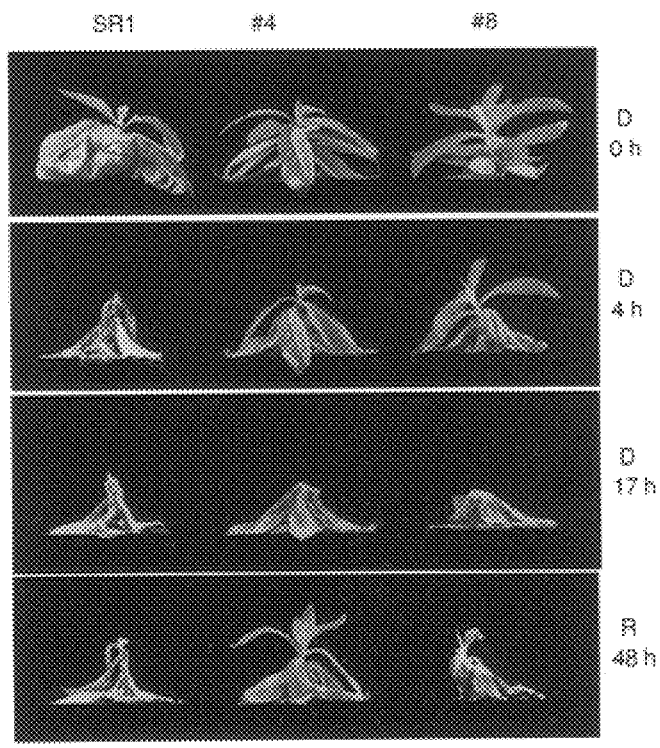
FIGS. 6A–6B. Drought survival of control and trehalose-producing tobacco plants. (A) Six to eight weeks' old in vitro propagated whole plants were exposed to air-drying (D) for the times indicated. After 17 h of stress-treatment, the nontransformed control plants (SR1) and trehalose-producing transgenic plants of lines 4 and 8 were rehydrated (R) by placing them in water. (B) Three week old seedlings of transgenic line 8 and both nontransformed (SR1) and vector-transformed (C) control plants were exposed to air-drying (D) for the times indicated. The seedlings were subsequently rehydrated (R) after 7 h of stress by placing them in water.

The protection by trehalose of excised leaves from drought injury indicated that trehalose could have a similar effect even at the whole plant level. To assess whether trehalose could enhance the drought tolerance of intact plants we exposed in vitro propagated whole plants to air drying (30% RH, FIG. 6A). Within 3 to 4 h the control plants had lost turgor and wilted. In contrast, the trehalose-producing transgenic plants only showed signs of turgor loss after prolonged air drying. After 17 hours of desiccation treatment the plants were rehydrated and the survival of the plants documented (FIG. 6A). Nontransformed control plants did not survive this treatment, as no recovery was detected even after prolonged rehydration. In contrast, trehalose-producing transgenic lines, although clearly wilted and having lost most of their tissue water (down to 30% residual fresh weight), survived 17 hours of desiccation.

Figure 6B:
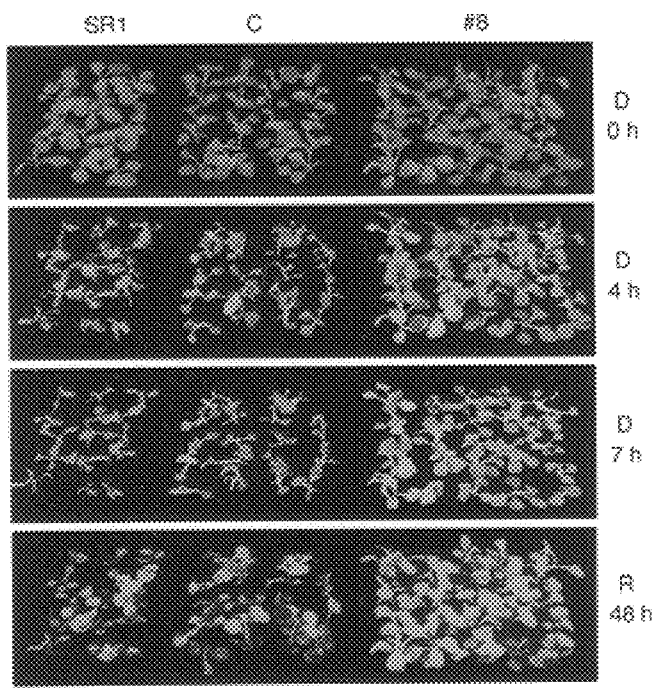

Enhanced drought survival was also manifested in young seedlings (FIG. 6B). Exposure of 3-week old seedlings from transgenic line 8 together with nontransformed and vector transformed control seedlings to air drying (50% RH) demonstrated clear differences in drought tolerance between the trehalose-producing and control plants. The transgenic trehalose-positive line 8 showed both delayed loss of turgor and enhanced survival of dehydration stress as compared with the control plants (FIG. 6B).

Example 4
Trehalose Production by Plants Co-transformed with a Gene Encoding a Tre6P Synthase and One or More Genes Encoding a Tre6Pase or Regulatory Polypeptide A person skilled in the art can prepare vectors containing the coding sequences of the yeast genes TPS2 and TSL1 under the control of the ats1A promoter and use them to transform tobacco, ArabidoPsis and other plants by the methods described in General Materials and Methods and Example 1. Plants simultaneously transformed with TPS1 and one or both of the other genes, TPS2 and TSL1, can be obtained by cross-breeding of individual transformants, by further transformation of one transformed plant with a second gene, or by transformation with vectors containing two or three of the genes linked to appropriate promoters: for example, TPS1 can be linked to the non-constitutive ats1A promoter, to provide control over trehalose synthesis, and the other gene(s) driven by constitutive promoters.

It is expected that the controlled expression of genes for two or more subunits of the yeast trehalose synthase complex, at least one being the 56 kDa subunit, will result in increased accumulation of trehalose in green tissues of the plant, because the 56 kDa subunit will be stabilised by the presence of the other subunit(s). Furthermore, introduction of the 102 kDa, Tre6Pase subunit will be beneficial because it will decrease the potential accumulation of Tre6P expected when the stability of the Tre6P synthase subunit is increased.

It is obvious that for this type of construction the TPS1 coding sequence can be replaced by the coding sequence of some other Tre6P synthase structural gene, the TPS2 sequence by that of some other Tre6Pase gene and the TSL1 sequence by that of some other gene encoding a polypeptide that confers regulatory properties or stability upon the Tre6P synthase and Tre6Pase in the same way as the TSL1 product confers such properties upon the other subunits of native yeast trehalose synthase.

Example 5
Transformation of Plants with Genes for Tre6P Synthase Under the Control of Stress-induced Promoters Plant promoters, such as LTI78 (Nordin et al [1993] Plant Mol. Biol. 21, 641–653) and RAB18 (Låang & Palva [1992] Plant Mol. Biol. 20, 951–962), are known that are induced in response to drought and cold stress. By transforming tobacco, Arabidoosis and other plants with the coding sequence of a gene for Tre6P synthase, such as TPS1 under the control of such a stress-induced promoter, alone or together with the coding sequences of genes for Tre6Pase or a regulatory polypeptide or both, such as TPS2 and TSL1 under the control of any convenient plant promoter, the accumulation of trehalose in plant tissues can be made to occur only in response to these stresses. The advantage is that levels of trehalose that might be deleterious to certain tissues of certain plants and which can also represent a yield-decreasing diversion of photo-synthetic capacity and possibly retard the growth of the plant, would accumulate only (1) when the plant is exposed fortuitously to stress (the benefits of the protection afforded by the trehalose then overcoming any deleterious effects) or (2) when the plant is deliberately exposed to stress in order to cause the accumulation of trehalose which will then be extracted from the harvested plant.

Example 6
Purification, Analysis and Cloning of Other Tre6P Synthases

Whereas there may be other metabolic routes to trehalose, it seems clear that the main synthetic pathway is via Tre6P, as described by Cabib & Leloir (1958, loc. cit.). The key enzyme in this pathway is Tre6P synthase, since, as disclosed above, once Tre6P has been made, many cells will be capable of dephosphorylating it to free trehalose. Thus, the key concept in the present invention is to introduce Tre6P synthase activity into the target plant. It is not of primary importance where this activity comes from. We have used the yeast enzyme, which happens to be a subunit of the yeast trehalose synthase complex, which contains at least two other subunits. In cases like this, it is possible that optimum activity of the Tre6P synthase subunit may require the presence of one or more of the other subunits, though evidently the 56 kDa Tre6P synthase subunit from yeast functions effectively in tobacco, without the 102 and 123 kDa subunits.

It is well known that enzymes catalysing the same reaction in widely different organisms are often homologous, so that once one member of the family has been cloned, the task of cloning other members is facilated. Since the yeast Tre6P synthase was cloned (Londesborough & Vuorio, [1992] U.S. patent application Ser. No. 07/836,021) it has become clear that there is a family of homologous proteins, including Tre6P synthase from *E. coli* and a protein from Methanobacterium thermoautotrophicum (McDougall et al, [1993] FEMS Microbiology Letters 107, 25–30). We decided to test whether other organisms also contained homologous Tre6P synthases.

*Mycobacterium smegmatis* contains a heparin-activated Tre6P synthase which has been partially purified and studied by Elbein's group (Liu et al, [1969] J. Biol. Chem. 244, 3728–3791; Lapp et al [1971] J. Biol. Chem. 246, 4567–4579; Elbein & Mitchell [1975] Arch. Biochem. Biophys. 168, 369–377; Pan et al, [1978] Arch. Biochem. Biophys. 186, 392–400). The enzyme purified by these workers had a specific activity of 0.8 U/mg protein at 37° C., with Glc6P and UDPG as substrates (the enzyme can use a spectrum of nucleoside-diphospho-glucose derivatives) and in the presence of optimal heparin. The preparation contained two polypeptides with SDS-PAGE molecular weights of about 45 and 90 kDa. We modified the authors' purification procedure by including protease inhibitors and other protein protecting agents in the buffers used, and adding a final chromatographic step in the presence of the non-ionic detergent, Triton X-100. Our final procedure was as follows:

1) *M. smegmatis* cells (28 g fresh weight grown for 3 days in Luria broth and stored frozen) were allowed to melt in 40 ml of 50 mM HEPES/KOH pH 7.5 containing 1 mM benzamidine, 2 mM $MgCl_2$, 1 mM EDTA, 1 mM dithiothreitol, 1 mM phenylmethylsulfonylfluoride (PMSF) and 10 µg pepstatin A/ml, and then broken in a French press. The homogenate was centrifuged for 20 min at 28000 g. $(NH_4)_2SO_4$ (30 g for every 100 ml) was added to the supernatant. The precipitated protein was collected, dissolved in 20 mM HEPES/KOH pH 7.5 containing 0.1 mM EDTA and 0.2 mM dithiothreitol (HED buffer) containing 1 mM PMSF and 10 µg pepstatin A/ml and dialysed overnight against HED buffer.

2) The dialysate was applied to a 3.4×25 cm column of DEAE-cellulose and the enzyme eluted at 20 ml/h with a linear gradient to 0.9 M NaCl in 1.2 1 of HED buffer. The peak enzyme fractions (at 0.2 M NaCl) were pooled (33 ml), and adjusted to 0.5 mM PMSF and 5 µg pepstatin A/ml. Protein was precipitated by addition of 9.9 g of $(NH_4)_2SO_4$ and dissolved in 50 mM Tris/HCl pH 7.5 containing 50 mM NaCl, 0.1 mM EDTA and 0.2 mM dithiothreitol (TNED buffer).

3) The dissolved proteins (3.7 ml) were run through a 2.8×34 cm column of Sephadex G100 equilibrated with TNED buffer at 36 ml/h. Peak enzyme fractions were immediately applied to a 1.5×8.5 cm column of Heparin Sepharose in TNED buffer. The column was developed with a gradient to 1.0 M NaCl in 100 ml at 5 ml/h. Enzyme eluted at about 0.5 M NaCl.

4) A sample of the Heparin Sepharose eluate (fraction H37 in Table 3) was transferred to TNED/0.1% (v/v) Triton X100 over a PM10 membrane in an Amincon cell and then applied to a 0.7×8 cm column of Heparin Sepharose equilibrated with TNED containing 0.1% (v/v) Triton X100 and eluted with a gradient to 1.0 M NaCl in 50 ml of the same buffer.

TABLE 3

Purification of Tre6P Synthase from *M. smegmatis*
Tre6P synthase was assayed as described by Londesborough and Vuorio (1993, loc. cit.) but at 35° C. and in the presence of 0.25 µg heparin/ml.

| Fraction | Volume (ml) | Sp. Activity (mU/mg) | Total Activity (U) |
| --- | --- | --- | --- |
| 28000 g Supernatant | 154 | 9 | 25.0 |
| Dialysed $(NH_4)_2SO_4$ precipitate | 52 | 21 | 35.2 |
| DE52 eluate | 33 | 139 | 23.4 |
| G100 eluate | 21 | 385 | 14.6 |
| First Heparin Sepharose eluate | | | |
| Fraction H33 | 2.7 | 1880 | 0.9 |
| Fraction H34 | 2.7 | 4380 | 2.1 |
| Fraction H35 | 2.7 | 6190 | 2.7 |
| Fraction H36 | 2.7 | 7890 | 2.8 |
| Fraction H37 | 2.7 | 6340 | 1.6 |
| Second Heparin Sepharose eluate (Only H37 applied) | | | |
| Fraction T21 | 1.4 | ND | 0.08 |
| Fraction T22 | 1.4 | ND | 0.14 |
| Fraction T23 | 1.4 | ND | 0.06 |

Figure 7:
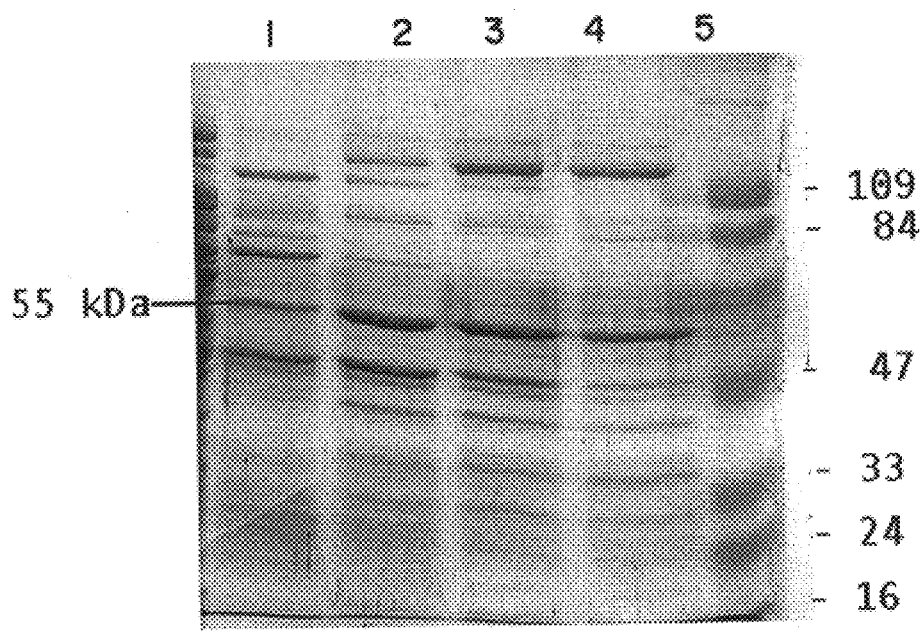
FIG. 7. SDS-PAGE analysis of fractions containing *M. smegmatis* Tre6P synthase eluted from the first Heparin-Sepharose column. Lanes 1 to 4 contain, respectively, samples of H33 (7.0 mU), H35 (20 mU), H36 (21 mU) and H37 (12 mU) (Table 3). After SDS-PAGE on 8% acrylamide, the gels were stained with Coomassie Brilliant Blue. The sizes of the molecular mass standards in lane 5 are shown in kDa. The position of the 55 kDa Tre6P synthase polypeptide is shown with an arrow.

Although the specific activities after the first Heparin Sepharose step were much higher than reported by Pan et al (1978), SDS-PAGE (FIG. 7) showed that these fractions were not pure. Surprisingly, a band at about 55 kDa was the only major band for which the intensity correlated well with enzyme activity. The 55 kDa band was excised and digested in the gel with trypsin and the tryptic peptides were separated by HPLC and sequenced as described (Londesborough and Vuorio, 1993 loc. cit.). Sequences are shown in Table 4 and in the Sequence Listings. For peptide peaks 29 and 31, which gave double sequences, the amino acids have been arbitrarily assigned to SEQ ID NOs 3 & 4 (from peak 29) and to SEQ ID NOs 6 & 7 (from peak 31) in the same way as shown in Table 4. The first 9 residues of Peptide 13 are 89% identical to residues 250–258 (VGAFPIGID; see Vuorio et. al., 1993 loc. cit.; EMBL accession no. X67499) of the 56 kDa Tre6P synthase from yeast.

TABLE 4

Amino acid sequences of internal tryptic peptides obtained from Tre6P synthase purified from *M. smegmatis*.

| Peptide Peak | Sequence | Sequence Listing |
| --- | --- | --- |
| 13 | VGAFPISIDSAEL | SEQ ID NO: 1 |
| 21 | AT/GFLDALAATGETGDSGVT | SEQ ID NO: 2 |
| 29 (double) | RVVVNNTSR | SEQ ID NO: 3 |
| | YLEGAR | SEQ ID NO: 4 |
| 25 | QVLAHDVDR | SEQ ID NO: 5 |
| 31 (double) | IGGAQPAD | SEQ ID NO: 6 |
| | VGALQVLL | SEQ ID NO: 7 |
| 43 | GEVQVGFR | SEQ ID NO: 8 |

Figure 8:
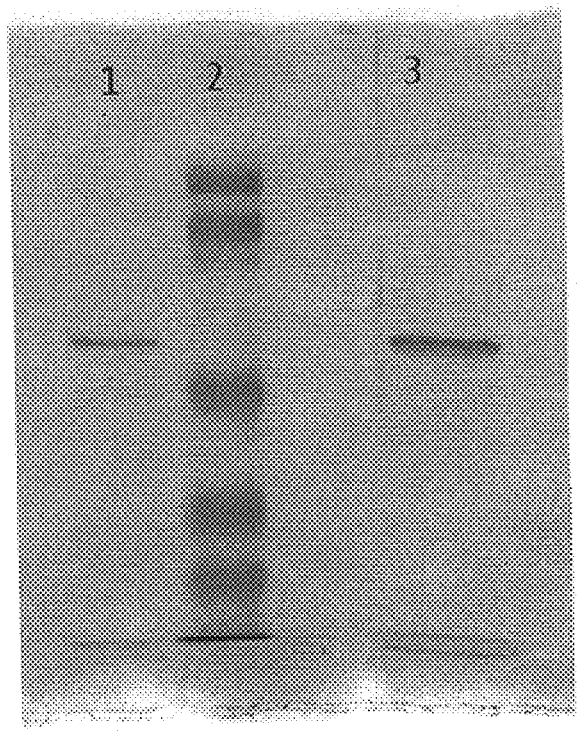
FIG. 8. SDS-PAGE analysis of the peak fraction of *M. smegmatis* Tre6P synthase eluted from the second Heparin-Sepharose column. Fraction T21 (Table 3) was concentrated in a Centricon 10 tube and then mixed with half its volume of 3-fold concentrated SDS-PAGE sample buffer. The overall concentration was 6-fold. Samples containing (lane 1) 2.9 mU and (lane 3) 8.7 mU of Tre6P synthase were subjected to SDS-PAGE on 8% acrylamide and stained with Coomassie Brilliant Blue. The molecular mass standards in lane 2 are, from top to bottom, 109, 84, 47, 33, 24 and 16 kDa.
Figure 9:
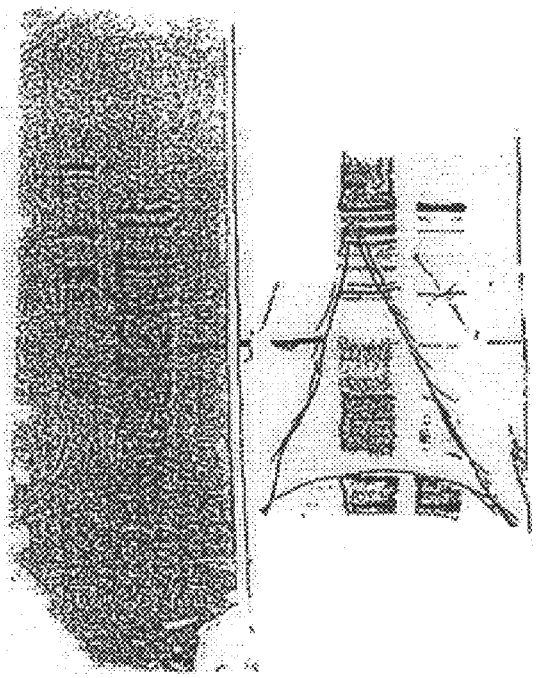
FIG. 9. Western analysis of Tre6P synthase purified from *M. smegmatis*. An 8% acrylamide gel was loaded with prestained molecular mass markers (lane 1: 200, 117, 80 and 47 kDa; lane 10: the only visible marker is 84 kDa), pure Tre6P synthase from fraction T21 (Table 3) (lanes 7 and 8: 2.9 mU; lanes 3,4 and 9: 8.7 mU) and the pooled active fractions from G100 Sephadex (Table 3) (lanes 6: 7.8 μg total protein; lanes 2 and 5: 23 μg total protein). After electrophoresis and blotting to nitrocellulose, the nitrocellulose membrane was cut between lanes 3 and 4 and between lanes 7 and 8. Lanes 1 to 3 were stained with Coomassie Brilliant Blue, lanes 4 to 7 were probed with anti-57 serum raised against the purified 56 kDa Tre6P synthase subunit from yeast and lanes 8 to 10 were probed with preimmune serum. Immunoreactive bands were visualised using goat anti-rabbit IgG-alkaline phosphatase conjugate from Promega according to the manufacturer's instructions, with colour development times of 2.8 minutes in both cases. The diagonal lines across lanes 4 to 7 are due to accidental creasing of the membrane during transfer to nitrocellulose.

To confirm that this about 55 kDa band represents the Tre6P synthase, further purification was attempted. The enzyme bound strongly to a UDP-glucuronate agarose column, but could not be recovered. Therefore, fraction H37 was transferred to a buffer containing 0.1% Triton X100 (two thirds of the activity was lost during this transfer) and rechromatographed on Heparin Sepharose in the presence of Triton X100. FIG. 8 shows that the about 55 kDa band was the only Coomassie blue reactive material present in the active fractions, apart from two faint bands smaller than cytochrome c. Evidently, the 90 kDa polypeptide reported by Pan et al (1978; loc. cit.) is not an essential component of this Tre6P synthase from *M. smegmatis*, and the size of the essential polypeptide, about 55 kDa, is notably bigger than that of the smaller, 45 kDa, component reported by these authors. FIG. 9 shows that this polypeptide is recognised by antiserum raised against the 56 kDa Tre6P synthase subunit of yeast trehalose synthase but not by pre-immune serum, showing that the Tre6P synthase of *M. smegmatis* shares antigenic determinants with the yeast enzyme. The nature of the other immunoreactive bands present in relatively crude preparations of the enzyme (see lanes 5 and 6 of FIG. 9) has not been investigated: not all of them are artefacts due to the large protein load, but represent related proteins. Nevertheless, the antiserum raised against the yeast enzyme can be used to detect and isolate positive clones from host cells transformed with a *M. smegmatis* gene bank. Similarly, the amino acid sequence data in Table 4 can be used to check the sequence of the isolated gene. The immunological and amino acid sequence similarities between the enzymes from yeast and *M. smegmatis* indicate that nucleotide probes designed from the TPS1 gene may also be successfully used to screen for the *M. smegmatis* gene.

In conclusion, immunological and sequencing studies of the *M. smegmatis* enzyme confirm that the Tre6P synthases from different organisms are members of a family. The genes of these enzymes may be used in the same way as TPS1 to make transgenic plants that synthesise trehalose and have improved stress-tolerance.

What is claimed is:

1. A plant transformed with the coding sequence of a heterologous gene encoding trehalose-6-phosphate synthase fused to a non-constitutive plant promoter so that the transformed plant synthesizes trehalose as a result of expression of the trehalose-6-phosphate synthase.

2. The plant of claim 1 wherein the plant promoter is tissue specific.

3. The plant of claim 1 wherein the plant promoter is light activated.

4. The plant of claim 1 wherein the plant promoter is activated by stress.

5. The plant of claim 1 wherein the gene encoding trehalose-6-phosphate synthase is microbial.

6. The plant of claim 5 wherein the trehalose-6-phosphate synthase gene is the yeast gene TPS1, encoding the 56 kDa subunit of yeast trehalose synthase.

7. The plant of claim 1 which is cotransformed with at least one gene encoding a trehalose-6-phophatase or a regulatory polypeptide that binds to trehalose-6-phosphate synthase or trehalose-6-phosphatase.

8. The plant of claim 7 wherein the gene encoding the trehalose-6-phosphatase is the yeast TPS2 gene and the gene encoding the regulatory polypeptide is the yeast TSL1 gene.

9. The plant of claim 6, wherein the plant promoter is ats1a.

10. The plant of claim 1 wherein the plant is more stress-tolerant than an untransformed plant.

11. The plant of claim 1 which is a muonocotyledonous plant.

12. The plant of claim 1 which is a dicotyledonous plant.

13. A process of producing trehalose comprising isolating trehalose from the plant of claim 1.

14. A seed produced by the plant of claim 1.

15. A method of increasing the trehalose content of a plant, comprising the steps of:

transforming a plant with a gene encoding trehalose-6-phosphate synthase operably linked to an inducible promoter, and cultivating the transformed plant under conditions that activate the inducible promoter.

16. The method of claim 15 wherein the gene is the yeast gene TPS1 encoding the 56 kDa subunit of yeast trehalose synthase.

17. A method of increasing the trehalose content of a plant comprising the steps of:

cotransforming a plant with a gene for trehalose-6-phosphate synthase under the control of a non-constitutive promoter, and with at least one gene for a trehalose-6-phosphatase or a regulatory polypeptide that binds to trehalose-6-phosphate synthase or trehalose-6-phosphatase under the control of a constitutive promoter or an inducible promoter, wherein the synthesis of trehalose is regulated by the expression of trehalose-6-phosphate synthase as controlled by the activity of the non-constitutive promoter, and cultivating the cotransformed plant under conditions that activate the non-constitutive promoter and the inducible promoter.

18. The method of claim 17 wherein the gene encoding the trehalose-6-phosphatase is the yeast TPS2 gene and the gene encoding the regulatory polypeptide is the yeast TSL1 gene.

19. The method of claim 15 wherein the inducible promoter causes expression specifically in storage organs.

20. The method of claim 15, wherein said inducible promoter is a stress-induced promoter.

21. The method of claim 20, wherein the transgenic plant accumulates trehalose in a storage organ.

22. The method of claim 21 wherein the plant is a root crop.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 13 amino acids
       (B) TYPE: amino acid
       (D) TOPOLOGY: Linear (ii) MOLECULE TYPE: Peptide (iii) HYPOTHETICAL: no (iv) FRAGMENT TYPE: N-terminal (v) SEQUENCE DESCRIPTION: SEQ ID NO:1:

Val Gly Ala Phe Pro Ile Ser Ile Asp Ser Ala Glu Leu
                 5                  10

(2) INFORMATION FOR SEQ ID NO:2:

(i) SEQUENCE CHARACTERISTICS:
       (A) LENGTH: 19 amino acids
       (B) TYPE: amino acid
       (D) TOPOLOGY: Linear (ii) MOLECULE TYPE: Peptide (iii) HYPOTHETICAL: no (iv) FRAGMENT TYPE: N-terminal (v) SEQUENCE DESCRIPTION: SEQ ID NO:2:

Ala Xaa Phe Leu Asp Ala Leu Ala Ala Thr Gly Glu Thr Gly Asp
                 5                  10                  15

Ser Gly Val Thr (2) INFORMATION FOR SEQ ID NO:3:

(i) SEQUENCE CHARACTERISTICS:
       (A) LENGTH: 9 amino acids
       (B) TYPE: amino acid
       (D) TOPOLOGY: Linear (ii) MOLECULE TYPE: Peptide (iii) HYPOTHETICAL: yes (iv) FRAGMENT TYPE: N-terminal (v) SEQUENCE DESCRIPTION: SEQ ID NO:3:

Arg Val Val Val Asn Asn Thr Ser Arg
                 5

(2) INFORMATION FOR SEQ ID NO:4:

(i) SEQUENCE CHARACTERISTICS:
       (A) LENGTH: 6 amino acids
       (B) TYPE: amino acid
       (D) TOPOLOGY: Linear (ii) MOLECULE TYPE: Peptide (iii) HYPOTHETICAL: yes (iv) FRAGMENT TYPE: N-terminal (v) SEQUENCE DESCRIPTION: SEQ ID NO:4:

Tyr Leu Glu Gly Ala Arg
                5

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: Linear (ii) MOLECULE TYPE: Peptide (iii) HYPOTHETICAL: no (iv) FRAGMENT TYPE: N-terminal (v) SEQUENCE DESCRIPTION: SEQ ID NO:5:

Gln Val Leu Ala His Asp Val Asp Arg
                5

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: Linear (ii) MOLECULE TYPE: Peptide (iii) HYPOTHETICAL: yes (iv) FRAGMENT TYPE: N-terminal (v) SEQUENCE DESCRIPTION: SEQ ID NO:6:

Ile Gly Gly Ala Gln Pro Ala Asp
                5

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: Linear (ii) MOLECULE TYPE: Peptide (iii) HYPOTHETICAL: yes (iv) FRAGMENT TYPE: N-terminal (v) SEQUENCE DESCRIPTION: SEQ ID NO:7:

Val Gly Ala Leu Gln Val Leu Leu
                5

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: Linear (ii) MOLECULE TYPE: Peptide (iii) HYPOTHETICAL: no -continued

```
    (iv) FRAGMENT TYPE: N-terminal (v) SEQUENCE DESCRIPTION: SEQ ID NO:8:

Gly Glu Val Gln Val Gly Phe Arg
```